United States Patent [19]

Young et al.

[11] Patent Number: 4,957,103
[45] Date of Patent: Sep. 18, 1990

[54] ORTHOPAEDIC BODY JACKETS

[75] Inventors: David E. Young, Watlington; Kenneth P. Davis, Hillington, both of England

[73] Assignee: Protectair Limited, Abingdon, England

[21] Appl. No.: 249,729

[22] Filed: Sep. 27, 1988

Related U.S. Application Data

[63] Continuation-in-part of Ser. No. 882,597, Jul. 7, 1986, Pat. No. 4,776,326.

[30] Foreign Application Priority Data

Oct. 14, 1987 [GB] United Kingdom ............... 8710080
Jun. 27, 1988 [GB] United Kingdom ............... 8815259

[51] Int. Cl.$^5$ .................................................. A61F 5/02
[52] U.S. Cl. .......................................... 128/78; 128/68
[58] Field of Search ................ 128/78, 75, 89 R, 87 R, 128/68

[56] References Cited

U.S. PATENT DOCUMENTS

| 2,322,119 | 10/1943 | Springer | 128/78 |
| 3,420,230 | 1/1969 | Ballard | 128/78 |
| 4,022,197 | 5/1977 | Castiglia | 128/78 |
| 4,202,327 | 5/1980 | Glancy | 128/78 |
| 4,481,941 | 11/1984 | Rolfes | 128/87 R |
| 4,531,515 | 7/1985 | Rolfes | 128/87 R |
| 4,559,933 | 12/1985 | Batard et al. | 128/88 |
| 4,569,340 | 2/1986 | Burton | 128/75 |
| 4,688,558 | 8/1987 | Hooper | 128/78 |
| 4,776,326 | 10/1988 | Young et al. | 128/80 F |

FOREIGN PATENT DOCUMENTS 0066028 12/1982 European Pat. Off. .

OTHER PUBLICATIONS

Orthopaedic Review, An Easier Way to make a Milwaukee Brace, vol. V, No. 2, Feb. 1976, pp. 47-52.

Primary Examiner—Edgar S. Burr
Assistant Examiner—Huong Q. Pham
Attorney, Agent, or Firm—Tilton, Fallon, Lungmus

[57] ABSTRACT

An orthopaedic body jacket including a semi-rigid thermoplastic shell adapted to be fitted and fastened around the abdomen of a patient. The shell has a constricted waist portion and outwardly flared upper and lower portions. An integrally moulded lateral portion extends upwardly from the flared lower portion and has an upper end protruding outwardly a substantial distance from the constricted waist portion. The lateral portion has a vertically-extending externally-facing channel that opens laterally outwardly from the shell and provides a straight, outwardly-facing planar surface for mounting an orthotic component in any of a plurality of positions of vertical adjustment.

8 Claims, 1 Drawing Sheet

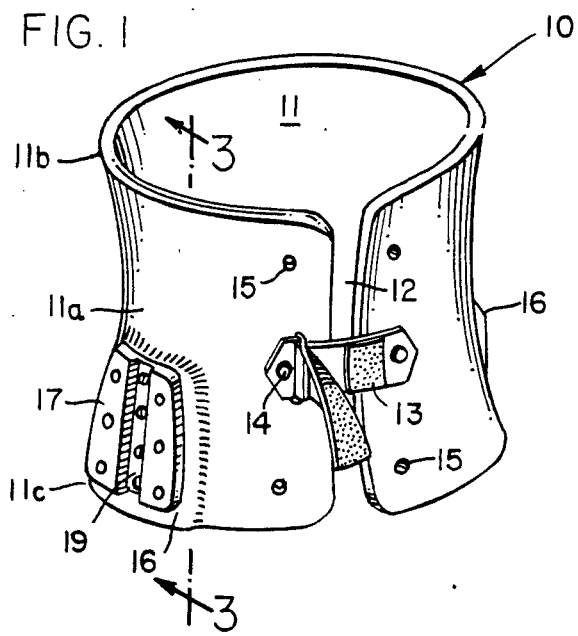
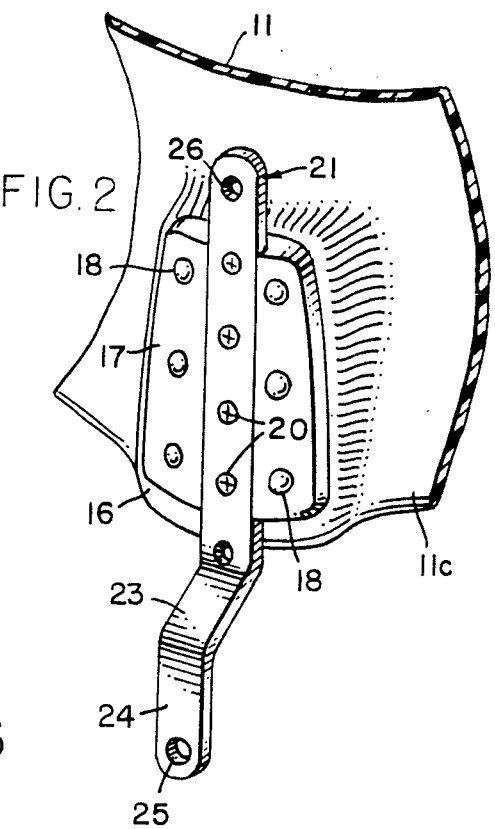
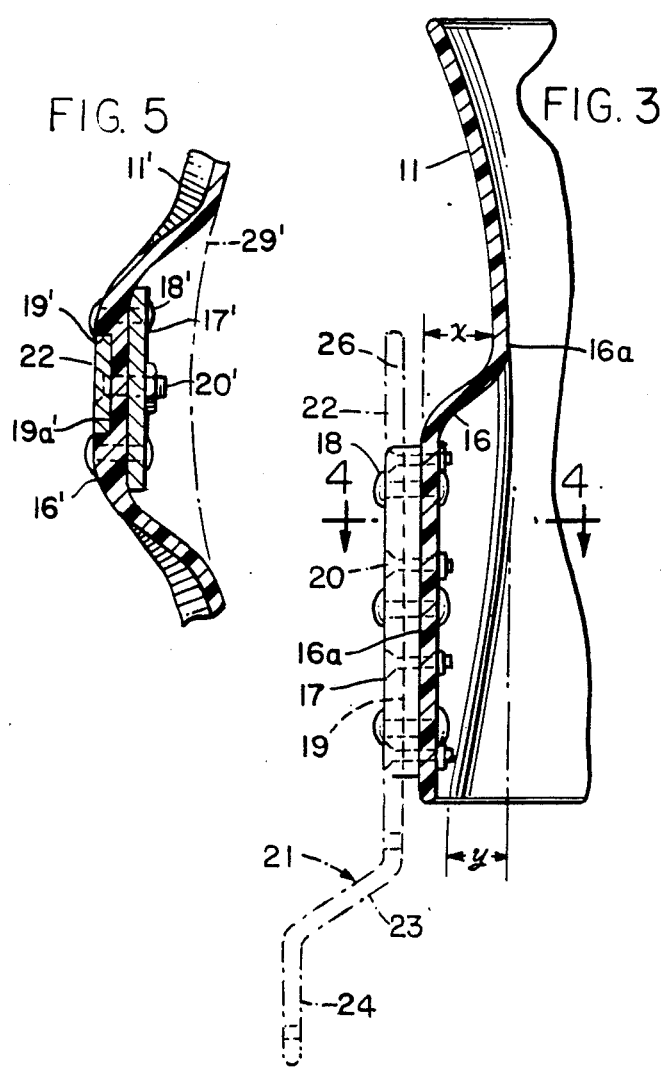
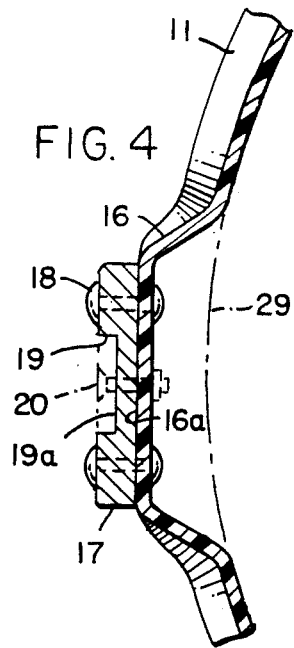

ORTHOPAEDIC BODY JACKETS

This application is a continuation-in-part of application Ser. No. 882,597, filed July 7, 1986 now U.S. Pat. No. 4,776,326.

This invention relates to orthopaedic body jackets and more especially to body jackets provided with means for mounting orthotic components such as leg calipers.

Body jackets used in the practice of orthotics have previously been constructed on an individual basis by contractors who are not hospital based. Generally, a thin Plaster of Paris cast is made of the patient's trunk and then split along the anterior and posterior midline for removal following which it is taken to the contractor's premises and a further positive cast is made of the internal surface. After surface imperfections have been removed by infilling, the internal case is used as a mould for a conventional vacuum forming process using thermoplastics sheets, for example 900 mm × 900 mm or 900 mm × 1200 mm and 3 to 6 mm thick, usually of medium density polyethylene or polypropylene at 140° to 180°C. After being cooled, the thermoformed body jacket shell is first roughly cut from the crude vacuum formed envelope and then trimmed more carefully. A conscientious contractor will then smooth the edges but this step is sometimes omitted. Occasionally, body jackets are lined, for example with a 3 mm or 5 mm thick layer of closed cell polyethylene foam or closed cell poly(ethylene/vinyl alcohol) foam, adhesively bonded to the jacket.

Although it is possible to laminate such foam liners directly to the thermoplastics sheet before vacuum forming the shell of the jacket, this is not popular. Prelaminated material also is not favoured. In both cases, the presence of the highly resilient liner precludes a vacuum tight seal during vacuum forming.

Straps are then fitted to the jacket shell in order to fasten it around the wearer's body and the finished body jacket is sent to the hospital or clinic. The patient is then called for a fitting which may be carried out by a technician or even by a representative of the contract or although, should the jacket prove unsatisfactory, it is highly unlikely that any significant modifications are possible at the hospital resulting in considerable delay before the jacket is finally supplied to the patient.

With children, the problem of delay is severe since children often develop so quickly that they can repeatedly outpace the supply system and in many cases never enjoy the benefits of a well fitting jacket. Also, children's body jackets will generally need to be replaced at intervals of six to nine months.

The prior art body jackets are very expensive due to their method of production which is slow, labour intensive and wasteful of materials. The material itself is hardly ideal since it allows no fine tuning in the body jacket on the patient at the fitting stage. All in all, the production method and the prior art body jackets are ill-conceived for the purpose they are supposed to serve.

The production process can also lead to poor quality in the finished article. If vacuum forming is carried out at the upper end of the working temperature range so that the plastics material is very soft and especially if the vacuum is applied rapidly, there is a real danger of thinning of the plastics material around the edges of the jacket. However, these are the very zones where the jacket is most required to provide support under compressive and bending loads.

Another shortcoming which is often not evident until after the body jacket has been accepted by the patient is the difficulty of attaching orthotic components, most of which are of metal. In these cases, the jacket is normally worn by the patient and the caliperage components are attached to the patient's leg. The two assemblies are then offered up to one another and an attempt is made to mark the desired mounting position on the jacket. It must be borne in mind here that a body jacket has compound curves and the hardware generally does not. Thus the conditions for poor fit of the resultant combination orthosis are very likely to be present.

Very few orthoses have either body jackets or a functionally equivalent structure formed more or less integrally with them. An example is the waist mounting of the Dur Fillauer Reciprocating Gait Orthosis which has marked antecedents in a similar device designed at the North West Orthotic Unit, Hope Hospital, Manchester and Salford University, Department of Engineering in the mid-1970s. These broad waistbands are not body jackets in any sense; they could not be isolated from the hardware and be used to treat low back pain, for example.

The present invention seeks to provide a body jacket in which there is provided means for easily and quickly mounting orthotic components such as caliperage items without the need for extensive reworking of the orthotic components.

The present invention seeks also to provide a standardised body jacket which may be produced simply and inexpensively and which may be easily and rapidly revised on the patient without expensive special equipment.

According to the invention, there is provided a body jacket comprising a semi rigid plastics shell adapted to be fitted and fastened around the abdomen of the patient, the shell having a moulded upstanding portion on at least one lateral outer surface carrying means to which an orthosis or brace component can be attached.

Body jackets according to the invention avoid many of the disadvantages associated with the prior art body jackets and have certain additional inherent advantages of their own which will become apparent from the following description.

Although the body jackets according to the invention are suitable for people of all ages, the initial development was carried out in the context of body jackets for children. For this, a large number of children was measured and standard anthropometric data sources were consulted. From these accumulated data, it was concluded that most children could be accommodated with seven basic sizes of body jacket although this did not include cases where significant spinal curvature or gross deformity was present.

A large number of casts was taken from actual children and from these, a basic blank shape was developed for each of the seven jacket sizes. Blanking tools were constructed to produce the blanks by die stamping. Since the largest jacket is for a 36 inch (900 mm) waist and is 12 inches (300 mm) deep, it will be understood that four body jacket blanks may be produced with virtually no waste from a plastics sheet 900 mm × 1200 mm. This is in contrast to the single prior art body jacket produced from a sheet of the same size.

Using a die cut blank enables a much smaller oven to be used for heating the plastics material prior to vacuum thermoforming, enables the softening time to be reduced and energy costs to be reduced in line with other savings. The die cut blanks may also incorporate holes made by punches in the cutting tool both for locating the blank accurately on the thermoforming mould and for fitting the straps and orthosis attachment means to the thermoformed shells.

Thermoforming moulds have been produced in hollow cast aluminum based on the same cast shapes as those used to produce the blanking tools. Each mould incorporates pegs to engage the locating holes in the blanks and flared top and bottom edges. The locating pegs ensure accuracy in the final body jacket shell and the flared edges ensure that the finished jacket will be comfortable to wear. Each mould incorporates also on one or both lateral aspects an upstanding portion, preferably of generally trapezoidal outline, in order to provide the required upstanding portion or portions on the lateral surface of the shell.

The lateral upstanding portions on the mould are, of course, reproduced in the resultant body jacket shell. The upstanding portions are preferably dimensioned such that their lateral extension is the same as or slightly greater than the distance between a vertical plane passing through the lower margin of the shell at the lateral mid-line and normal to it, and another vertical plane passing through the most waisted part of the shell also at the lateral mid-line and normal to it. The proximal extension of the upstanding portion is preferably to slightly above the most waisted part of the shell and distally the upstanding portion extends to the lower edge of the shell.

A single upstanding portion may be formed on only one lateral surface of the shell if such an arrangement is preferred but this carries the penalty of doubling inventory requirements. Generally, therefore, upstanding portions will be provided on both lateral surfaces of the shell.

According to one aspect of the invention, the thermoplastics blanks used to form the body jacket shell are punched in the area of the upstanding portions with a regular series of small holes. A plate, referred to below as a matrix plate, with a series of holes identical to that in the surface of the upstanding portion, is then attached to the inner surface of the shell for example, by adhesive bonding, so that the holes are in alignment. The matrix plate is suitably of steel and the holes in it are preferably threaded.

In another aspect of the invention, a moulded matrix plate is attached to the outside of the upstanding portion for example, by screwing or rivetting, thus dispensing with the need for adhesives. Any protruding parts of the rivets or screws on the inner surface are, of course, effectively held away from the body of the wearer of the finished jacket by virtue of being within the recess behind the upstanding portion.

The matrix plate serves to provide a mounting for calipers or other orthotic hardware with much greater ease and speed than was previously possible. An upper arm on a rigid splint or caliper having a suitably spaced series of holes can be very readily attached to a body jacket according to the invention incorporating a matrix plate and good accuracy in fitting may be achieved. Furthermore, unlike prior art body jackets, the attachment points for such hardware may be readily revised thus reducing the frequency with which jackets need to be replaced, for example as the child develops.

Although the body jackets can be lined before or after thermoforming with poly(ethylene/vinly alcohol) foam which can be die cut to shape and attached to the inner surface of the shell, for example with double sided adhesive tape, it is preferred to supply the jacket in an unlined state and for the patient first to cover his abdomen with a separate moisture permeable liner. In this way, rucking of the material is avoided and patient comfort is maximised.

The present invention is described below in greater detail by way of example only with reference to the accompanying drawings, in which:

FIG. 1 is perspective view of a body jacket according to the invention;

FIG. 2 is an enlarged view of part of the body jacket shown in FIG. 1, illustrating the matrix plate and an attached caliper arm;

FIG. 3 is an enlarged vertical sectional view taken along line 3—3 of FIG. 1;

FIG. 4 is an enlarged horizontal sectional view taken along line 4—4 of FIG. 3; and FIG. 5 is an enlarged horizontal sectional view similar to FIG. 4 but illustrating a further embodiment of this invention.

Referring to FIG. 1 of the drawings, there is shown a body jacket 10 according to the invention. The principal component of the jacket is a shell 11 moulded of semirigid thermoplastic sheet material, for example of polyethylene having a thickness of about 5 mm, which has been vacuum formed on a suitable mould to produce the characteristic waisted shape similar to that of known body jackets. More specifically, the shell includes a constricted waist portion 11a and outwardly flared upper and lower portions 11b and 11c. Although the plastics material is sufficiently rigid for the shell to be self supporting and to provide in use the required degree of support for the patient wearing the body jacket, it nevertheless has sufficient flexibility for it to be opened out in order to be placed around the waist of the patient. For this purpose, the shell 11 is open at 12 along its ventral mid-line, with two front portions of the shell along the two sides of the opening being fastened by suitable loop and pile straps 13 (of which only one is shown for clarity) attached to the sides of the opening 12 by means of rivets 14. The rivets pass through holes 15 formed in the plastics blank or sheet from which the shell is formed.

As can be seen in FIG. 1, the lateral surface of the shell has an integrally-moulded upstanding lateral portion 16 adjacent its lower edge. This portion is generally trapezoidal in shape and is formed during the vacuum-forming step by which the shell is produced. Referring to FIG. 3, it will be observed that the upstanding lateral portion 16 defines a generally vertical outer surface 16a that is displaced laterally outwardly from the contoured outer surface of the remainder of the body jacket. Means are provided along the vertical surface 16a for mounting an orthotic component 21 in any of a variety of vertical positions of adjustment. In the embodiment depicted in FIGS. 1-4, such means constitutes a rigid matrix plate 17 attached to the shell by rivets 18, or by any other suitable fastening means, which pass through holes formed in the plastics blank from which the shell is produced. The matrix plate may be formed of any material of high strength and rigidity such as rigid plastics or metal.

Passing generally vertically along the outer surface of the matrix plate 17 is a channel 19 having a laterally-facing and substantially vertically-extending planar surface 19a (FIG. 4). The channel 19 is vertically elongated and of substantially uniform width throughout its length (height). A vertical series of uniformly-spaced openings are formed in the channel for receiving screws 20, such screws being threaded into captive nuts recessed into the back of the matrix plate or into the shell behind the matrix plate. Alternatively, the screw-receiving holes of the matrix plate may be threaded.

Although only one matrix plate is visible on the body jacket in FIG. 1, an identical matrix plate may be mounted on a similar upstanding portion 16 on the other lateral surface of the shell, if desired, in addition to or instead of the matrix plate shown in FIG. 1.

In the embodiment illustrated, the orthotic component 21 takes the form of a caliper arm mounted in the channel 19 of the matrix plate 17 and attached thereto by screws 20. The caliper arm is of metal, for example stainless steel, and is of generally cranked configuration having a straight upper arm portion 22, an intermediate offset portion 23, and a lower attachment portion 24. The lower attachment portion 24 has a pivot hole 25 by means of which the arm can be pivotally connected to the remainder of the orthotic device. The straight upper arm portion 22 has a series of uniformly-spaced openings or holes 26, the spacing between such openings being such that they are alignable with the openings and screws 20 of the matrix plate. In the illustration given, the elongated upper arm portion 22 has a series of six such openings 26, only four of which are depicted as being used for mounting the arm on the matrix plate. With screws 20 removed, the upper arm portion 22 is vertically slidable along channel 19 into any of a plurality of positions of adjustment with screws 20 then passing through two or more selected openings 26 to lock the orthotic component 21 in position.

It will be observed that the upstanding lateral portion 16 is dimensioned so that its lateral extension "x" is the same or slightly greater than the distance "y" between a vertical plane passing through the lower margin of the shell at the lateral mid-plane and normal to it, and another vertical plane passing through the most waisted part of the shell also at the lateral mid-line and normal to it. The proximal extension 16a of the upstanding portion is preferably slightly above the most waisted (i.e., the most constricted) part of the shell and distally the upstanding lateral portion 16 extends to the lower edge of shell 11 (FIG. 3).

The recess in the interior lateral surface of the body jacket behind the upstanding portion 16 safely accommodates the rear faces of the rivets 18 and the screws 20 and their associated nuts, but may nevertheless house a pad of foamed plastics material to provide additional protection for the patient wearing the jacket. While such pad is omitted from the drawings for clarity of illustration, the contour of its inner surface is depicted by phantom line 29 in FIG. 4.

In the embodiment described above, the planar and generally vertical surface for adjustably supporting the orthotic component 22 is the surface 19of matrix plate 17. In the modified construction of FIG. 5, the vertical channel 19' is formed directly in the outer surface of the upstanding lateral portion 16'. The straight arm portion 22 of orthotic component 21 is abdomen of a patient; said shell having a cont slidably received within channel 19' and is secured in place in any selected position of vertical adjustment by screws 20' in the manner already described. A rigid, reinforcing matrix plate 17' is shown to be secured to the interior surface of the shell, within the recess defined by upstanding lateral portion 16', by means of rivets 18'. If desired, that recess may be filled with plastics foam 29' although, as clearly depicted in FIG. 5, the heads of rivets 18' and screws 20' are disposed well within the recess out of possible contact with a wearer.

It will be apparent that by manufacturing body jackets according to the invention incorporating the features described above, the waste which occurs with prior manufacturing methods is substantially eliminated. Minimal finishing is necessary after the shell has been vacuum formed, generally only trimming of the edges of the shell and riveting on of the straps and of the matrix plate or plates.

Although the body jackets described above are intended for patients having little or no spinal curvature, for example, children suffering from Legg-Calve-Perthes disease, it is possible also to produce body jackets according to the invention for patients with idiopathic scoliosis of considerable severity. This can be achieved by manufacturing a special thermoforming mould from a negative cast taken from the individual patient.

It is also possible according to the invention to form the body jacket from a shell which is split also along the dorsal mid-line. The two half shells may then be joined with two or three adjustable dorsal straps. Such an arrangement may be useful where greater precision is required in positioning the orthotic components.

We claim:

1. An orthopaedic body jacket comprising a semi-rigid thermoplastic shell adapted to be fitted and fastened around the abdomen of a patient; said shell having a constricted waist portion and outwardly flared upper and lower portions; said shell having a pair of front portions defining a ventral opening therebetween and being sufficiently flexible to permit said front portions to be flexed apart when fitting said shell about the waist of a wearer; said shell also having an integrally mounded upstanding lateral portion; said lateral portion extending upwardly from said flared lower portion and having an upper end protruding outwardly a substantial distance from said constricted waist portion; means along said upstanding lateral portion defining a generally verticallyextending externally-facing channel that opens laterally outwardly away from said shell and having a straight, outwardly-facing, planar surface for mounting an orthotic component in any of a plurality of positions of vertical adjustment; sand externally-facing channel being of substantially uniform width throughout its length.

2. The jacket of claim 1 in which an orthotic component has a rigid, straight arm portion slidably received in said channel for vertical sliding movement into selected positions of adjustment; and locking means releasably securing said arm portion against movement within said channel.

3. The jacket of claim 2 in which said locking means comprises a first series of uniformly-spaced openings in said arm portion; a second series of uniformly-spaced openings in said channel alignable with the openings of said arm portion; and fastening means extendable through at least two pair of aligned openings in said first and second series for anchoring said arm portion in a selected position of adjustment.

4. The jacket of claims 1, 2, or 3 in which said channel is formed in said upstanding lateral portion.

5. The jacket of claim 4 in which a rigid matrix plate is secured to said shell along an interior surface of said upstanding lateral portion.

6. The jacket of claim 1 in which said means defining said laterally-facing external channel comprises a rigid matrix plate exteriorly secured to said upstanding lateral portion.

7. The jacket of claim 6 in which an orthotic component has a rigid, straight arm portion slidably received in said channel for vertical sliding movement into selected positions of adjustment; and locking means releasably securing said arm portion against movement within said channel.

8. The jacket of claim 7 in which said locking means comprises a first series of uniformly-spaced openings in said arm portion; a second series of uniformlyspaced openings in said channel alignable with the openings of said arm portion; and fastening means extending through at least two pair of aligned openings of said first and second series for anchoring said arm portion in a selected position of adjustment.

* * * * *